| United States Patent [19] | [11] | 4,077,844 |
|---|---|---|
| Marshall et al. | [45] | Mar. 7, 1978 |

[54] PROCESS FOR PREPARING STEFFIMYCINOL

[75] Inventors: Vincent P. Marshall, Portage; David W. Elrod, Kalamazoo; James M. Koert, Kalamazoo; Elizabeth A. Reisender, Kalamazoo; Paul F. Wiley, Kalamazoo, all of Mich.

[73] Assignee: The Upjohn Company, Kalamazoo, Mich.

[21] Appl. No.: 782,621

[22] Filed: Mar. 30, 1977

[51] Int. Cl.² ............................................. C12D 9/18
[52] U.S. Cl. ............................................. 195/80 R
[58] Field of Search ..................................... 195/80 R

[56] References Cited

U.S. PATENT DOCUMENTS

| 3,590,028 | 6/1971 | Arcamone et al. ............... 195/80 R |
| 3,976,667 | 8/1976 | Kelly .................................... 260/365 |

OTHER PUBLICATIONS

Biochemistry, vol. 15, pp. 4139–4145, (1976).
The Journal of Antibiotics, Oct. 1975, vol. 28, No. 10, pp. 838–840.

Primary Examiner—Alvin E. Tanenholtz
Attorney, Agent, or Firm—Roman Saliwanchik

[57] ABSTRACT

Bioconversion of the antibiotic steffimycinone to the antibiotic steffimycinol. Steffimycinol is active against various microorganisms, for example, *Bacillus subtilis, Mycobacterium avium* and *Streptococcus pyogenes*. Steffimycinol is converted to 7-deoxysteffimycinol by a microaerophilic *Aeromonas hydrophila* fermentation. 7-Deoxysteffimycinol is active against *Sarcina lutea, Bacillus cereus,* and *B. subtilis*. Thus, there antibiotics can be used to inhibit the growth of the above microorganisms in various environments.

3 Claims, No Drawings

PROCESS FOR PREPARING STEFFIMYCINOL

The invention herein was made in the course of, or under Contract NO1-CM-43753 with the National Cancer Institute, National Institutes of Health, Bethesda, Md. 20014.

BACKGROUND OF THE INVENTION

The process for preparing the antibiotic steffimycinone and the description of its various biological properties are disclosed in U.S. Pat. No. 3,976,667.

The structure of steffimycinone can be shown as follows:

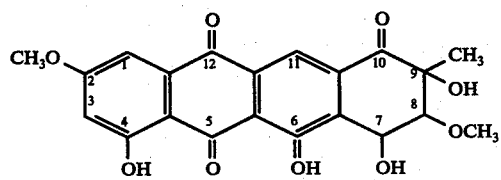

Steffimycinol and 7-deoxysteffimycinol can be prepared by reduction of steffimycinone as disclosed in co-pending U.S. application Ser. No. 775,856, filed on Mar. 9, 1977. Steffimycinol and 7-deoxysteffimycinol have the following structures:

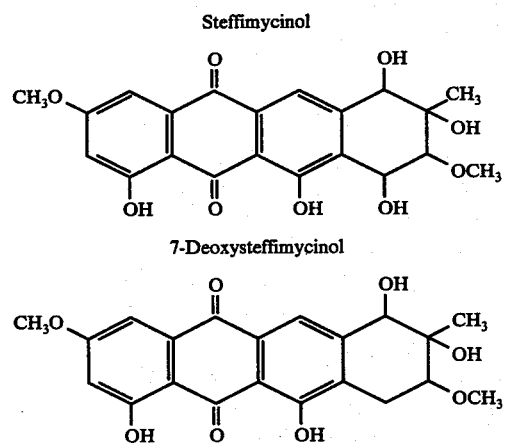

Both antibiotics are biologically active, as disclosed above, and can be used in various environments to inhibit the growth of susceptible microorganisms. For example, steffimycinol and 7-deoxysteffimycinol can be used for treating breeding places of silkworms, to prevent or minimize infections which are well known to be caused by *Bacillus subtilis*. 7-Deoxysteffimycinol can be used in papermill operations to control the contamination of wool by the microorganism *Bacillus cereus*. Steffimycinol can be used to control *Mycobacterium avium* which is a known producer of generalized tuberculosis in birds and rabbits.

Also pertinent in the background of the subject invention is the article entitled "Reductive Microbial Conversion of Anthracycline Antibiotics" appearing in Biochemistry (1976), Vol. 15, pages 4139–4145, and the article entitled "Microbial Conversion of Anthracycline Antibiotics" appearing in The Journal of Antibiotics (October, 1975), Vol, 28, No. 10, pages 838–840. These articles disclose the microbial conversion of various anthracycline antibiotics, including steffimycin and steffimycinone. The reduction product of steffimycin being 7-deoxysteffimycinone and that for steffimycinone being 7-deoxysteffimycinone. There is no disclosure or suggestion in these publications of the processes of the subject invention.

BRIEF SUMMARY OF THE INVENTION

Steffimycinol can be prepared by the 10-keto reduction of steffimycinone. This biological process is catalyzed by aerobically grown *Streptomyces peucetius* var. caesius or *Streptomyces nogalater*, and by crude enzyme preparations of *S. nogalater*.

7-Deoxysteffimycinol can be prepared by the reductive conversion of steffimycinol. This process involves in microaerophilic fermentation using the microorganism *Aeromonas hydrophila*.

DETAILED DESCRIPTION

The Microorganisms

*Streptomyces peucetius* var. *caesius* is a known microorganism deposited at the American Type Culture Collection in Washington, D.C. Its accession number is ATCC 27952. A subculture of this microorganism can be obtained from this repository upon request. This microorganism is characterized in U.S. Pat. No. 3,590,028. This characterization is incorporated herein by reference thereto.

*Streptomyces nogalater* var. *nogalater* is a known microorgansim deposited at the Northern Regional Research Laboratory, U.S. Department of Agriculture, Peoria, Ill., U.S.A. Its accession number is NRRL 3035. A subculture of this microorganism can be obtained from this repository upon request. This microorganism is characterized in U.S. Pat. No. 3,183,157. This characterization is incorporated herein by reference thereto.

A subculture of the microorganism *Aeromonas hydrophila* strain 2c has been deposited at the Northern Regional Research Laboratory, U.S. Department of Agriculture, Peoria, Ill., U. S. A. Its accession number is NRRL B-11099. A subculture of this microorganism can be obtained from this repository upon request. The taxonomic description of *Aeromonas hydrophila*, NRRL B-11099, follows.

It has the morphological characteristics of the Genus Aeromonas [Schubert, R.H.W. 1974. *Genus* II. Aeromonas Kluyver and van Niel 1936. p. 345–348. In R. E. Buchanan and N. E. Gibbons (ed.), Bergey's manual of determinative bacteriology, 8th ed. The Williams & Wilkons Co., Baltimore][Schubert, R.H.W. 1968. The Taxonomy and Nomenclature of the Genus Aeromonas. Kluyver and van Niel 1936. Int. J. Syst. Bact. 18: 1–7]. Aeromonas is placed in Part 8, Gram-Negative Facultatively Anaerobic Rods, Family II Vibrionaceae, Genus II in Bergey's Manual 8th Edition, supra.

Micromorphological Characteristics

The strain deposited as NRRL B-11099 is motile and Gram-negative. The cells are straight, rod-shaped with rounded ends, to coccoid. They occur singly, in pairs, or short chains. The rods measure 1.0 by 1.6–2.9 μm. The cells are motile by polar flagella occurring singly or paired. Occasionally a lateral flagellum is noted.

Cultural and Biochemical Characteristics

The strain is a facultative anaerobe which has colorless growth on nutrient agar at 28° C. Biochemical characteristics are given in Table 1.

Neotype Strain

*Aeromonas hydrophila* subsp. hydrophila ATCC 7966 [see: Schubert, R.H.W. 1974. *Genus* II. Aeromonas Kluyver and van Niel 1936. p. 345–348. In R. E. Buchanan and N. E. Gibbons (ed.), Bergey's manual of determinative bacteriology, 8th ed. The Williams & Wilkins Co., Baltimore].

TABLE 1

| Biochemical Characteristics Of A. hydrophila strain 2C | |
|---|---|
| Test For | Reaction |
| beta-galactosidase | + |
| arginine dihydrolase | ++ |
| lysine decarboxylase | + |
| ornithine decarboxylase | − |
| assimilation (Simmon's) | ± |
| H$_2$S | − |
| urease (Ferguson) | − |
| deamination | − |
| indole | + |
| acetoin (VP) | ++ |
| proteolyse | ++ |
| acidification (glucose) | + |
| acidification (mannitol) | + |
| acidification (inositol) | − |
| acidification (sorbitol) | − |
| acidification (rhamnose) | − |
| acidification (sucrose) | − |
| acidification (melibiose) | − |
| acidification (amygdalin) | + |
| acidification (arabinose) | +. |
| oxidase | + |
| nitrate reduction | + |
| catalase | + |

The above tests were run using the API 20 Enterobacteriaceae (API 20E) System (Analytab Products Inc., Carle Place, New York, N.Y. 11514).

The bioconversions of the subject invention are carried out by growing the disclosed microorganisms in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distiller's solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation medium since tap water and unpurified ingredients are used as components of the medium prior to sterilization of the medium.

The bioconversion processes can be effected at any temperature conducive to satisfactory growth of the particular microorganism, for example, between about 18° and 40° C., and preferably between about 20° and 28° C. The medium normally remains neutral during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the bioconversion process and the attendant inefficient utilization of the equipment. Accordingly, it is desirable to produce a vegetative inoculum in a nutrient broth culture by inoculating this broth culture with an aliquot from a soil stock, an agar plug stored above liquid N$_2$, or a slant culture. When a young, active vegetative inoculum has thus been secured, it is transferred aseptically to large vessels or tanks. The medium in which the vegetative inoculum is produced can be the same as, or different from, that utilized for the bioconversion process, so long as good growth of the microorganism is obtained.

A variety of procedures can be employed in the isolation and purification of the compounds produced by the subject invention, for example, solvent extraction, partition chromatography, silica gel chromatography, liquid-liquid distribution in a Craig apparatus, adsorption on resins, and crystallization from solvents.

In a preferred recovery process the compounds are recovered from the culture medium by separation of the mycelia and undissolved solids by conventional means, such as by filtration or centrifugation. The antibiotic is recovered from the filtered or centrifuged broth by extraction with a suitable solvent for the antibiotic. The solvent extract containing the desired antibiotic is concentrated and then subjected to purification procedures as disclosed infra.

After recovery of the antibiotic from the bioconversion fermentation beer, the recovery preparation is then subjected to purification procedures which will ultimately yield a purified crystalline preparation of the antibiotic.

The crude preparation of the antibiotic can be subjected to chromatographic procedures on silica gel. The chromatographic column can be eluted with a suitable solvent system, for example, CHCl$_3$—MeOH (97:3).

Active fractions from the above chromatographic procedure can be subjected to another similar chromatographic procedure to obtain the antibiotic in its essentially pure form.

The following examples are illustrative of the processes of the subject invention but are not to be construed as limiting. All percentages are by weight and all solvent mixture proportions are by volume unless otherwise noted.

EXAMPLE 1

Bioconversion Of Steffimycinone To Steffimycinol

Part A. Fermentation

An agar slant of *Streptomyces peucetius* var. caesius, ATCC 27952, is used to inoculate a series of 500-ml Erlenmeyer flasks, each containing 100 ml of sterile seed medium consisting of the following ingredients:

Brewer's Yeast: 3 g/liter
Peptone: 5 g/liter
Ca(NO$_3$)$_2$.4 H$_2$0: 0.5 g/liter
Tap water q.s.: 1 liter The seed medium presterilization pH is 7.8. The seed inoculum is grown for about 40 hours at 25° C. on a Gump rotary shaker operating at 250 r.p.m. and having a 2 ½ inch stroke.

Seed inoculum (inoculation rate is 5%), prepared as described above, is used to inoculate a series of 500-ml Erlenmeyer flasks each containing 100 ml of sterile medium consisting of the following ingredients:

Glucose monohydrate: 20 g/liter
Tryptone: 5 g/liter
Yeast Extract: 3 g/liter
Tap water: Balance The inoculated medium is incubated at a temperature of 25° C. for 2 days while being agitated at a rate of 400 r.p.m. and aerated at a rate of 10 standard liters per minute with a back pressure of 10 psig.

After 2 days incubation, 25 mg/l steffimycinone is added aseptically to the medium.

The bioconversion is monitored by thin layer chromatography (tlc) at intervals between 0.5 and 3 days after initial steffimycinone addition. Harvest is usually after 3 to 7 days after addition of the steffimycinone.

The seed culture age of the above S. peucetius var. caesius process can range from 24 to 96 hours. The production culture age at the time of steffimycinone addition can also range from 24 to 96 hours. The fermentation conversion is generally complete in 3 days, though this period can range from 1 to 7 days. The temperature of the S. peucetius var. caesius fermentation can range from 18° to 37° C., with the preferred temperature being 25° C.

Seed media which can be used in place of the above medium are nutrient agar, supplemented inorganic salts agar (PAS — having the following composition per liter:

$K_2HPO_4$, 4.4 g; $KH_2PO_4$, 1.7 g; $NH_4Cl$, 2.1 g; $MgSO_4.7H_2O$, 39 mg; $FeSO_4.7H_2O$, 1.1 mg; $CaCl_2.2H_2O$, .33 mg; NaCl, .01 mg; $Na_2MaO_4.2H_2O$, .5 mg; $MnSO_4.H_2O$, 5.6 mg; Agar, 20 g; and sufficient distilled $H_2O$ to bring volume to 1 liter), and the like. Fermentation media which can be used in the above process are nutrient broth, supplemented inorganic salts broth, TYG per liter (Tryptone, 5 g; Yeast Extract, 3 g; glucose, 20 g; and sufficient distilled $H_2O$ to bring volume to 1 liter), and the like.

Steffimycinone can be added to this fermentation as a dimethylformamide solution (25 mg/ml) or as a milled aqueous suspension to a final concentration in the range of 1–100 mg/l, with the preferred amount being 25 mg/l.

Part B. Recovery

Fermentation beer, as described above, to which 200 mg of steffimycinone has been added is filtered. The filtrate is extracted with three 1.71 l portions of methylene chloride. The combined extracts are evaporated under reduced pressure to an oily residue. The residue is dissolved in 100 ml of methylene chloride which is washed with two 50-ml portions of $H_2O$. The combined water washes are washed with 50 ml of methylene chloride which is added to the original extracts. The combined organic solution is dried ($MgSO_4$), filtered and evaporated under reduced pressure to a dry residue (wt 388 mg). The residue is dissolved in 3 ml of $CHCl_3$—MeOH (97:3). The ppt which forms is removed by filtration (wt 91 mg). The filtrate is chromatographed by HPLC (High Performance Liquid Chromatography) using a 60-g porosil A column and the above solvent system and collecting 3 ml fractions. On the basis of tlc using $CHCl_3$—MeOH (95:5, $R_f$ 0.19) fractions 70–120 are combined. Evaporation under reduced pressure gives 73 mg which is again chromatographed as above using a 15.5 g column. From this is obtained 20 mg which is combined with the above ppt and recrystallized from $CH_3OH$. The yield of crystalline material is 68 mg. This is identified as steffimycinol by tlc in $CHCl_3$—MeOH (95:5), $^{13}C$ NMR spectrum and analysis (Calcd. for $C_{21}H_{20}O_9$: C, 60.57, H, 4.84. Found: C, 60.55; H, 4.97).

EXAMPLE 2

Bioconversion Of Steffimycinone To Steffimycinol

Part A. Fermentation

An agar slant of *Streptomyces nogalater* var. nogalater, NRRL 3035, is used to inoculate a series of 500-ml Erlenmeyer flasks, each containing 100 ml of sterile seed medium consisting of the following ingredients:

Brewer's Yeast: 3 g/l
Peptone: 5 g/l
$Ca(NO_3)_2 . 4H_2O$: 0.5 g/l
Tap water q.s.: 1 liter The seed medium presterilization pH is 7.8. The seed inoculum is grown for about 40 hours at 25° C. on a Gump rotary shaker operating at 250 r.p.m. and having a 2 ½ inch stroke.

Seed inoculum (inoculation rate is 5%), prepared as described above, is used to inoculate a series of 500-ml Erlenmeyer flasks each containing 100 ml of sterile medium consisting of the following ingredients:

Glucose monohydrate: 20 g/liter
Tryptone: 5 g/liter
Yeast Extract: 3 g/liter
Tap water: Balance The inoculated medium is incubated at a temperature of 25° C. for 2 days on a Gump rotary shaker operating at 250 r.p.m. and having a 2 ½ inch stroke.

After 2 days incubation, 10 mg/l steffimycinone is added aseptically to the medium. Another addition of steffimycinone (50 mg/l) is made 15 hours later.

The bioconversion is monitored by tlc at intervals between 0.5 and 3 days after initial steffimycinone addition. Harvest is usually after 3 to 7 days after addition of the steffimycinone.

The seed culture age of the above S. nogalater var. nogalater process can be the same as described for S. peucetius var. caesius. The first steffimycinone can be added to the S. nogalater var. nogalater fermentation at any time between 24 and 96 hours of fermentation time. The second addition of steffimycinone can be made sometime between 40 and 96 hours of fermentation time. Advantageously, this addition can be made at approximately 63 hours of fermentation time.

The time for the S. nogalater var. nogalater seed and fermentation phases can range from 18° to 37° C., with the preferred temperature being 25° C.

The seed and fermentation media for S. nogalater var. nogalater can be the same as described above for S. peucetius var. caesius. The concentration of steffimycinone added to the fermentation also can be the same as described above for the S. peucetius var. caesius.

Part B. Recovery

Fermentation beer, as described above, to which 1 g of steffimycinone has been added is mixed with 240 g of filter aid and filtered. The filter cake is washed with 1.2 l of water. The filtrate (5.6 l) is extracted with four 1.4-l portions of $CHCl_3$. The extracts are combined and evaporated under reduced pressure to give 828 mg of residue which is chromatographed on 83 g of silica gel eluting with $CHCl_3$—MeOH (97:3) until one hundred and sixty 10-ml fractions have been collected. A tlc analysis using $CHCl_3$—MeOH (9:1; $R_f$ 0.45) indicates that fractions 49-90 contain steffimycinol. Fractions 49-65 are combined as being purer material and are evaporated under reduced pressure to give 195 mg of steffimycinol identified by tlc comparison with an authentic sample using the above solvent system. Fractions 60-90 are combined and evaporated under reduced pressure, yield; 257 mg. This material is combined with 120 mg of material previously obtained by a similar procedure. The total material is deposited on 2 g of silica gel which is added to a column of 38 g of silica gel packed in $CHCl_3$—MeOH (98:2). The column is eluted with the same solvent system collecting eighty-six 5-ml fractions. On the basis of a tlc analysis as above fractions 50-70 are combined and evaporated under reduced pressure to give 182 mg. A small portion is recrystallized from $CH_3OH$, mp 238°-240° (Dec); mass spectrum (m/e) 416. A tlc comparison in $CHCl_3$—MeOH (9:1) indicates identity with authentic steffimycinol.

EXAMPLE 3

Bioconversion Of Steffimycinone With Cell-Free Extract

Part A. Preparation of S. nogalater var. nogalater, NRRL 3035, Cell-Free Extract Five to 10 g of whole S. nogalater var. nogalater, NRRL 3035, are suspended in 0.1 M potassium phosphate, pH 7.4, containing 0.01 M β-mercaptoethanol. The suspension is sonicated 5 minutes in the cold using a Raytheon 10 kc sonic oscillator. The resultant material is centrifuged in the cold for 15 minutes at $10^4 \times g$. The supernatant fluid is used as the cell-free extract.

Part B. Cell-Free Conversion Of Steffimycinone To Steffimycinol

The following describes the composition of the reaction mixture per ml; steffimycinone, 0.5 mg; TPNH (Triphosphopyridine nucleotide — reduced form), 1.0 mg; cell-free extract, 10 mg; potassium phosphate, pH 7.4, 100 μmoles; β-mercaptoethanol, 10 μmoles, and sufficient $H_2O$ to bring the final volume to 1.0 ml. The reaction mixture which is placed on a reciprocal shaker is incubated for 24 hours at 25° C.

The above reaction time can vary from 3 to 96 hours. The temperature range can vary from 18° to 37° C.

The pH of the buffer can vary from 5 to 10 and other buffers, for example, Tris, Glycine, $Na_2CO_3$, and Na Borate can be used.

Steffimycinone can be added to the reaction as a dimethylformamide solution at a concentration of 25 mg/ml. This can then give a final concentration in the reaction of approximately 100 mcg/ml. This final concentration can range from 25-500 mcg/ml.

Part C. Recovery

A 75 ml fermentation using S. nogalater var. nogalater, NRRl 3035, cell-free extract, described above, to which 75 mg of steffimycinone was added, is mixed with about 4 g of filter aid and filtered. The filter cake is washed with about 20 ml of water. The filter cake is extracted with five 25-ml portions of $CHCl_3$, and the filtrate is extracted with four 50-ml portions of $CHCl_3$. Combination and evaporation of the filter cake extracts gives 117 mg of residue. The same procedure with the filtrate extracts gives 17 mg. The two materials are combined and chromatographed on a 20 cm × 10 cm preparative thin layer plate having a 1 mm coating of silica gel and using $CHCl_3$—MeOH (95:5) as the developing system. Three bands are obtained. The middle band is removed and eluted with $CHCl_3$—MeOH (95:5) to give 66 mg of material identified as steffimycinone by tlc using cyclohexane-ethyl acetate-ethanol (5:3:2) and $CHCl_3$—MeOH—$H_2O$ (78:20:2). The slowest moving band is isolated by the same procedure, yield; 17 mg. It is found to be homogeneous by tlc and have the same $R_f$ as steffimycinol in the above two solvent systems as well as in the solvent systems $CHCL_3$-MeOH (95:5) and methyl ethyl ketone-acetone-water (70:20:11), mass spectrum (m/e) 416.

EXAMPLE 4

Bioconversion Of Steffimycinol To 7-deoxysteffimycinol

Part A. Fermentation

An agar slant of Aeromonas hydrophila, NRRL B-11099, is used to inoculate a series of 500-ml Erlenmeyer flasks, each containing 100 ml of sterile seed medium consisting of the following ingredients:

Tryptone: 3 g/liter
Yeast Extract: 5 g/liter
Glucose: 20 g/liter
Tap water q.s.: 1 liter The seed medium presterilization pH is 6.9. The seed inoculum is grown for about 24 hours at 25° C. without shaking.

Seed inoculum (inoculation rate is 5%), prepared as described above, is used to inoculate a series of 4000 ml reagent bottles each containing 4000 ml of sterile medium consisting of the following ingredients per liter: Yeast Extract, 1 g; Nutrient Broth, 2 g; $K_2HPO_4$, 4.4g; $KH_2PO_4$, 1.7 g; $NH_4Cl$, 2.1 g; $MgSO_4.7H_2O$, 39 mg; $FeSO_4.7H_2O$, 1.1 mg; $CaCl_2.2H_2O$, .33 mg; NaCl, 0.11 mg; $Na_2MoO_4.2H_2O$, 0.5 mg; $MnSO_4.H_2O$, 5.6 mg; and sufficient distilled $H_2O$ to bring final volume to 1 liter.

Steffimycinol (50 mg/l), as a milled aqueous suspension or dimethylformamide solution, is added aseptically at the time of inoculation.

The inoculated medium in the sealed reagent bottles is incubated at a temperature of 25° C. for 7 days with no air space remaining following inoculation.

The seed culture age of the A. hydrophila process in Part A can range from 12 to 72 hours. The fermentation can be conducted from about 48 hours to 2 weeks. The temperature range for the seed and fermentation phases of A. hydrophila can range from 18° to 42° C., with the preferred temperature being 25° C.

The seed and fermentation media for A. hydrophila can be varied as disclosed above for S. peucetis var. caesius, Example 1, Part A.

Steffimycinol is added to the fermentation medium as a milled aqueous suspension of dimethylformamide solution (50 mg/ml) to a final concentration of 50 mg/l. A higher concentration can be used, i.e. in the range of 5-300 mg/l.

Part B. Recovery

An 8 l microaerophilic *A. hydrophila* fermentation, as described above, in which the substrate has been 250 mg of steffimycinol, if filtered. Both filtrate and the filter paper are extracted with 2 l portions of methylene chloride. The combined extracts are evaporated to dryness under reduced pressure leaving 262 mg of residue. The residue is deposited on 1.5 g of silica gel which is added to a column of 26 g of silica gel packed in $CHCl_3$—MeOh (98:2). The column is developed with the same solvent system collecting one hundred and thirty-five 5-ml fractions. On the basis of tlc using $CHCl_3$—MeOH (9:1, $R_f$ 0.61) fractions 28-34 are combined. Evaporation under reduced pressure gives 62 mg of 7-deoxysteffimycinol identified by tlc comparison with an authentic sample and by a mass spectrum (m/e 400).

The microorganism *Streptomyces peucetius* var. caesius, as disclosed in U.S. Pat. No. 3,590,028 — Column 1, has also been deposited at the Institute of Microbiology of the Rutger University (U.S.A.) receiving the index number I.M.R.U. 3920 and at the Institute of Milan (Italy) receiving the index number I.P.V. 1946.

We claim:

1. A process for preparing the antibiotic steffimycinol which comprises cultivating *Streptomyces peucetius* var. caesius, having the identifying characteristics of ATCC 27952, in an aqueous nutrient medium under aerobic conditions in the presence of the antibiotic steffimycinone until substantial conversion of steffimycinone to steffimycinol, and recovering steffimycinol.

2. A process, according to claim 1, wherein steffimycinone is present in the fermentation medium in a concentration of about 1 to about 100 mg/l.

3. A process, according to claim 2, wherein 25 mg/l of steffimycinone is added to the fermentation medium at about 2 days after inoculation.

* * * * *